United States Patent [19]
Horwell et al.

[11] Patent Number: 5,998,435
[45] Date of Patent: Dec. 7, 1999

[54] USE OF A TACHYKININ ANTAGONIST FOR THE MANUFACTURE OF A MEDICAMENT FOR THE TREATMENT OF EMESIS

[75] Inventors: David Christopher Horwell; John Hughes, both of Cambridge; Martyn Clive Pritchard; Lakhbir Singh, both of Cambridgeshire, all of United Kingdom

[73] Assignee: Warner-Lambert Company, Morris Plains, N.J.

[21] Appl. No.: 09/194,620

[22] PCT Filed: Jun. 18, 1997

[86] PCT No.: PCT/US97/10503

§ 371 Date: Dec. 1, 1998

§ 102(e) Date: Dec. 1, 1998

[87] PCT Pub. No.: WO97/49393

PCT Pub. Date: Dec. 31, 1997

Related U.S. Application Data

[60] Provisional application No. 60/021,030, Jun. 26, 1996.

[51] Int. Cl.$^6$ .................................................. A61K 31/40
[52] U.S. Cl. .................................................. 514/310
[58] Field of Search .................................................. 514/419

[56] References Cited

U.S. PATENT DOCUMENTS

| 5,360,820 | 11/1994 | Hagan et al. | 514/559 |
| 5,594,022 | 1/1997 | Horwell et al. | 514/419 |

FOREIGN PATENT DOCUMENTS

| 9506645 | 3/1995 | WIPO . |
| 9508549 | 3/1995 | WIPO . |

*Primary Examiner*—Raymond Menley, III
*Attorney, Agent, or Firm*—Elizabeth M. Anderson

[57] ABSTRACT

The instant invention is directed to a method for the treatment of emesis comprising administering the compound [R,S]-[2-(1H-Indol-3-yl)-1-methyl-1-(1-phenyl-ethylcarbamoly)-ethyl]-carbamic acid benzofuran-2ylmethyl ester.

7 Claims, 13 Drawing Sheets

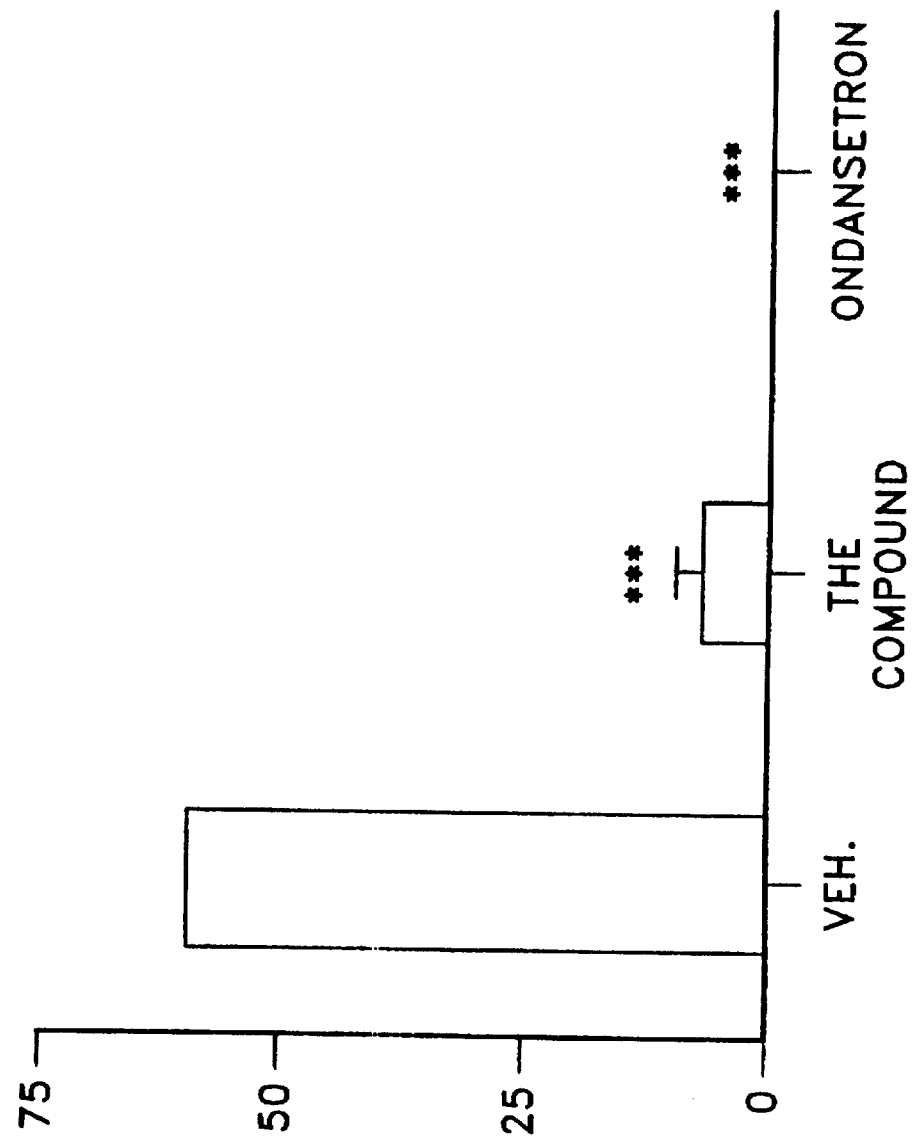

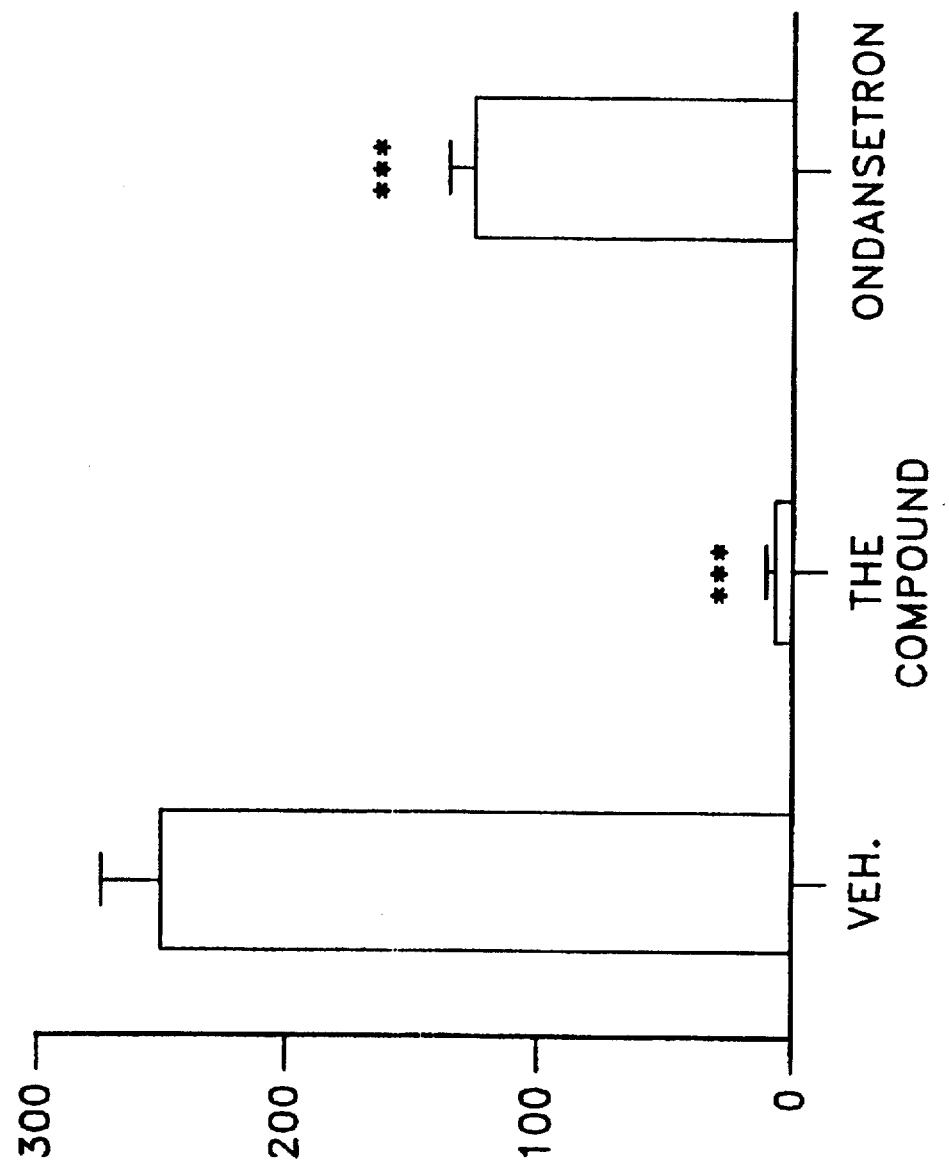

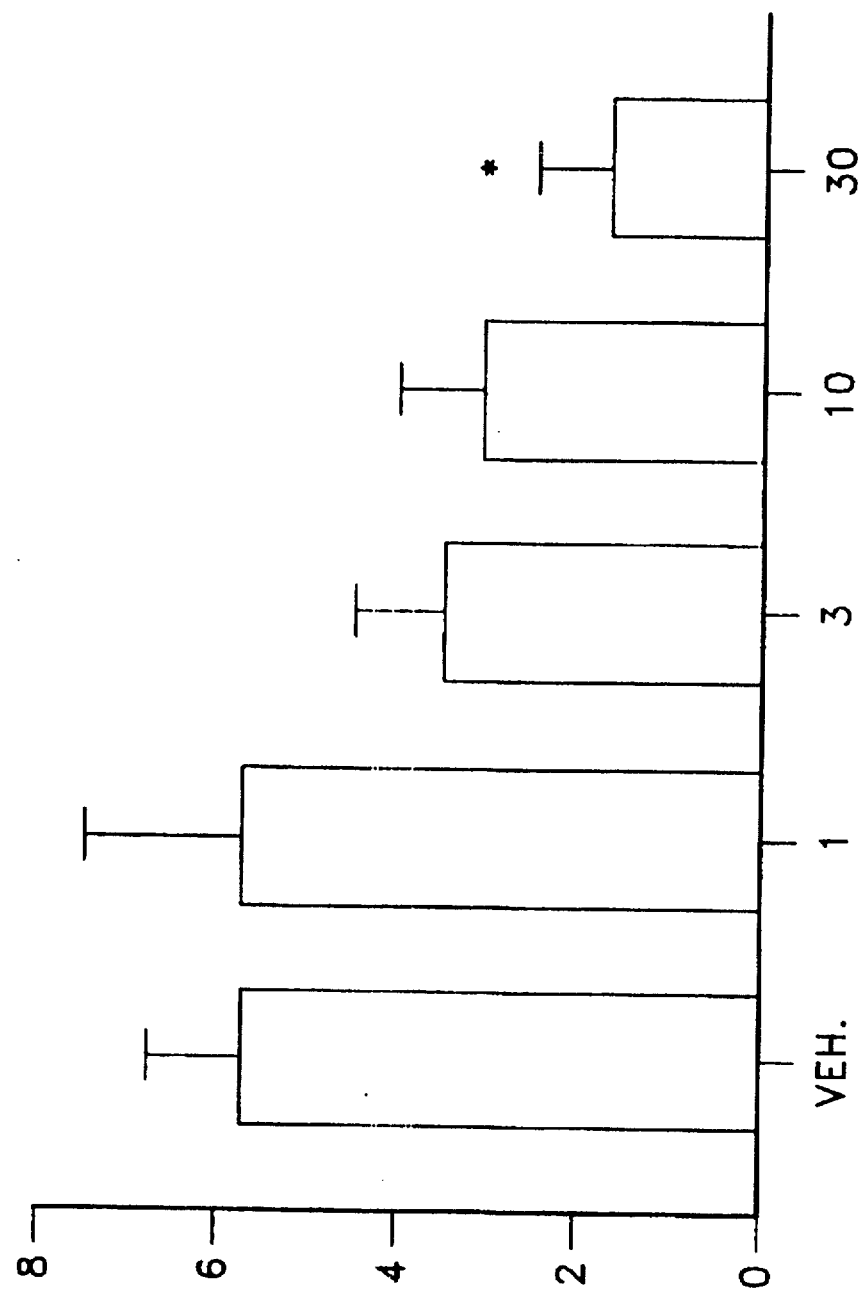

USE OF A TACHYKININ ANTAGONIST FOR THE MANUFACTURE OF A MEDICAMENT FOR THE TREATMENT OF EMESIS

This application claims priority over provisional application 60/021,030 filed Jun. 26, 1996 and is a 371 of PCT/US97/10503 filed Jun. 18, 1997.

BACKGROUND OF THE INVENTION

Nausea and vomiting are distressing symptoms associated with a variety of conditions such as motion sickness, pain, and a number of gastrointestinal disorders. Emesis also occurs in a number of clinical situations such as following cancer chemotherapy and surgery under general anaesthesia. The impact of these symptoms on the quality of life of sufferers is severe, so much so in the case of cancer chemotherapy as to have a significant impact on compliance.

Although the emergence of 5-HT$_3$ receptor antagonists has had an impact on the treatment of emesis induced by anti-cancer therapy, their major effects are confined to the acute phase of the response. Anti-cancer drugs induce acute emesis via actions in the gut, specifically the release of 5-HT which activates receptors on abdominal vagal afferents. This is wholly consistent with the observations that 5-HT$_3$ antagonists have a relatively restricted anti-emetic profile. Thus, these compounds are less effective against the delayed emesis observed following cancer chemotherapy, post-operative emesis, muscarinic receptor agonists, and erythromycin.

NK$_1$ receptor antagonists have been shown to possess a broad anti-emetic spectrum, have a different site of action, and provide the best opportunity to date of an antiemetic therapy which will be effective against a wide range of emetogenic compounds and conditions. U.S. Pat. No. 5,360,820.

Treatment of emesis is intended to include prophylaxis as well as the alleviation of established symptoms.

The treatment of emesis includes the treatment of nausea, retching, and vomiting. Emesis includes acute emesis, delayed emesis, and anticipatory emesis. For example, emesis may be induced by drugs such as cancer chemotherapeutic agents such as alkylating agents, e.g. cyclophosphamide, carmustine, lomustine, and chlorambucil; cytotoxic antibiotics, e.g. dactinomycin, doxorubicin, mitomycin-C, and bleomycin; antimetabolites, e.g. cytarabine, methotrexate, and 5-fluorouracil; vinca alkaloids, e.g. etoposide, vinblastine, and vincristine; and others such as cisplatin, dacarbazine, procarbazine, and hydroxyurea; and combinations thereof; radiation sickness; radiation therapy, e.g. irradiation of the thorax or abdomen, such as in the treatment of cancer; poisons; toxins, such as toxins caused by metabolic disorders or by infection, e.g. gastritis; pregnancy; vestibular disorders, such as motion sickness; post-operative sickness; gastrointestinal obstruction; reduced gastrointestinal motility; visceral pain, e.g. myocardial infarction or peritonitis; migraine; increased intercranial pressure; decreased intercranial pressure (e.g. altitude sickness); and opioid analgesics, such as morphine.

SUMMARY OF THE INVENTION

The instant invention is a method for the treatment of emesis which comprises administering a therapeutically effective amount of a compound named [R,S]-[2-(1H-Indol-3-yl)-1-methyl-1-(1-phenyl-ethylcarbamoyl)-ethyl]-carbamic acid benzofuran-2-ylmethyl ester (The Compound) to said mammal.

The method is for acute emesis, delayed emesis, emesis induced by a cancer-chemotherapeutic, and emesis induced by cisplatin during both the acute and delayed phases. The Compound is also useful in the treatment of motion sickness and in post-operative nausea and vomiting or clinical situations following surgery.

BRIEF DESCRIPTION OF THE DRAWINGS

FIG. 2. Effect of The Compound on cisplatin-induced acute and delayed emesis in the ferret. Cisplatin (5 mg/kg) was administered i.p., The Compound (10 mg/kg, i.p., tid), ondansetron (1 mg/kg, i.p., tid), or PEG-200 was administered i.p. three times a day (first dose was given 1 hour before cisplatin). Results are shown as the mean number of vomits and retches (vertical bars show SEM) in 6 animals per group. P<0.005, *P<0.0001 Significantly different from the vehicle treated control group.

FIG. 2a is Day 1 (acute emesis 0–3 hours);

FIG. 2c is Day 2 (24–48 hours).

FIG. 4. Effect of The Compound on apomorphine-induced emesis in the ferret. The Compound was administered mg/kg i.p. 1 hour before apomorphine (0.25 mg/kg, s.c.). Animals were observed for the following 1 hour. Results are shown as the mean of 9–14 animals per group (vertical bars show SEM). *P<0.05 Significantly different from the vehicle treated control group (ANOVA followed by Dunnett's t-test).

FIG. 4a, 4b, and 4c are vomits, retches, and episodes, respectively.

FIG. 5. Effect of The Compound on copper sulphate-induced emesis in the ferret. The Compound was administered mg/kg i.p. 1 hour before copper sulphate (12.5 mg/kg, p.o.). Animals were observed for the following 2 hours. Results are shown as the mean of 8–14 animals per group (vertical bars show SEM). *P<0.05, **P<0.01 Significantly different from the vehicle treated control group (ANOVA followed by Dunnett's t-test).

DETAILED DESCRIPTION

[2-(1H-Indol-3-yl)-1-methyl-1-(1-phenyl-ethylcarbamoyl)-ethyl]-carbamic acid benzofuran-2- ylmethyl ester (The Compound) is a selective, high affinity ligand at the human $NK_1$ receptor. It binds with nanamolar affinity to $NK_1$ recognition sites present in human cell line, guinea pig, dog, ferret, and hamster brain. It is an antagonist found to be useful in the treatment of emesis (nausea and vomiting) induced by chemotherapy and other emetogens. The Compound has an excellent pharmacokinetic profile and it readily penetrates into the central nervous system.

Since The Compound has good duration of action, it is possible to administer it two times per day. The Compound has good bioavailability and therefore can be given orally. This is an advantage for patients who are at home and no longer receive drug intravenously.

The Compound has the chemical structure

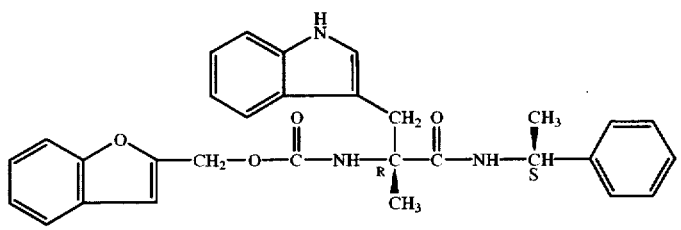

The Compound, synthetic procedures for its preparation, and certain uses are taught in U.S. Pat. No. 5,594,022 issued Jan. 14, 1997. The patent is hereby incorporated by reference.

Effect of The Compound on Cisplatin-Induced Emesis in the Ferret

Recent clinical data suggests that there are two distinct phases of chemotherapy-induced emesis. The acute (Day 1) emesis is sensitive to antagonism by $5-HT_3$ receptor antagonists and is differentiated from subsequent or delayed response that shows a greater resistance to control with $5-HT_3$ receptor antagonists. The potential antiemetic activity of the selective $NK_1$ receptor antagonist The Compound was evaluated in the ferret model of acute and delayed emesis to cisplatin.

Acute Phase

Adult male albino Fitch ferrets (>1 kg weight) were individually housed with free access to food (SDS Diet "C", Special Diet Services Ltd, Essex, U.K.). Thirty minutes prior to the commencement of the studies, the ferrets were presented with 100 g of commercially available tinned cat food.

Figure 1:
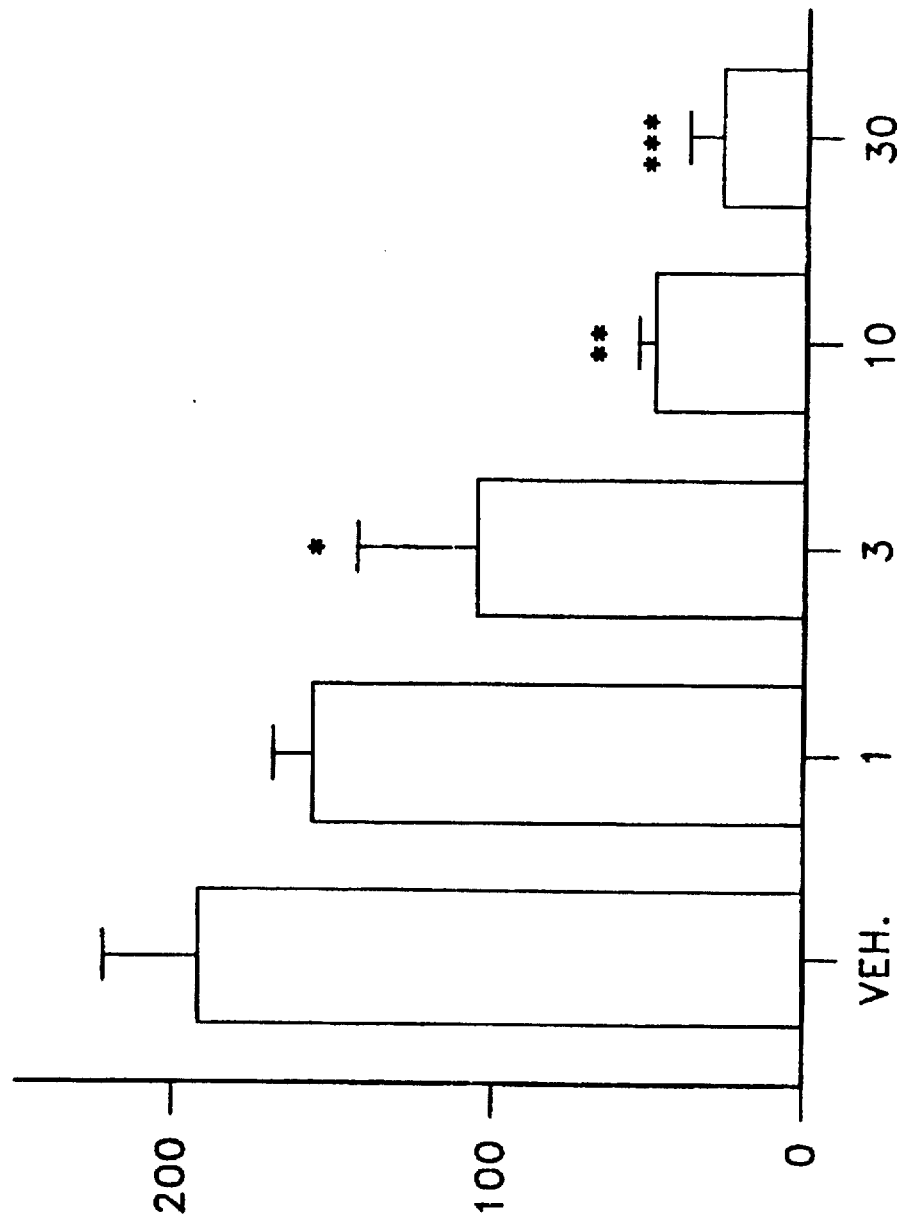
FIG. 1. Effect of The Compound on cisplatin-induced acute emesis in the ferret. Cisplatin (10 mg/kg, i.p.) was administered 1 hour before The Compound (i.p.) or vehicle (PEG-200). Results are shown as the mean number of vomits and retches for the first 4-hour observation period (vertical bars show SEM) in 4 animals per group. *P<0.05, P<0.01, and *P<0.001 Significantly different from the vehicle treated control group.

The Compound administered i.p. (in PEG-200 vehicle) 1 hour before a high dose of cisplatin (10 mg/kg, i.p.) dose-dependently (3–30 mg/kg) reduced the frequency of vomiting and retching during the 4-hour observation period with a minimum effective dose of 3 mg/kg (FIG. 1). At 30 mg/kg, The Compound produced a complete antagonism of the emetic response (FIG. 1).

Delayed Phase

Figure 2B:
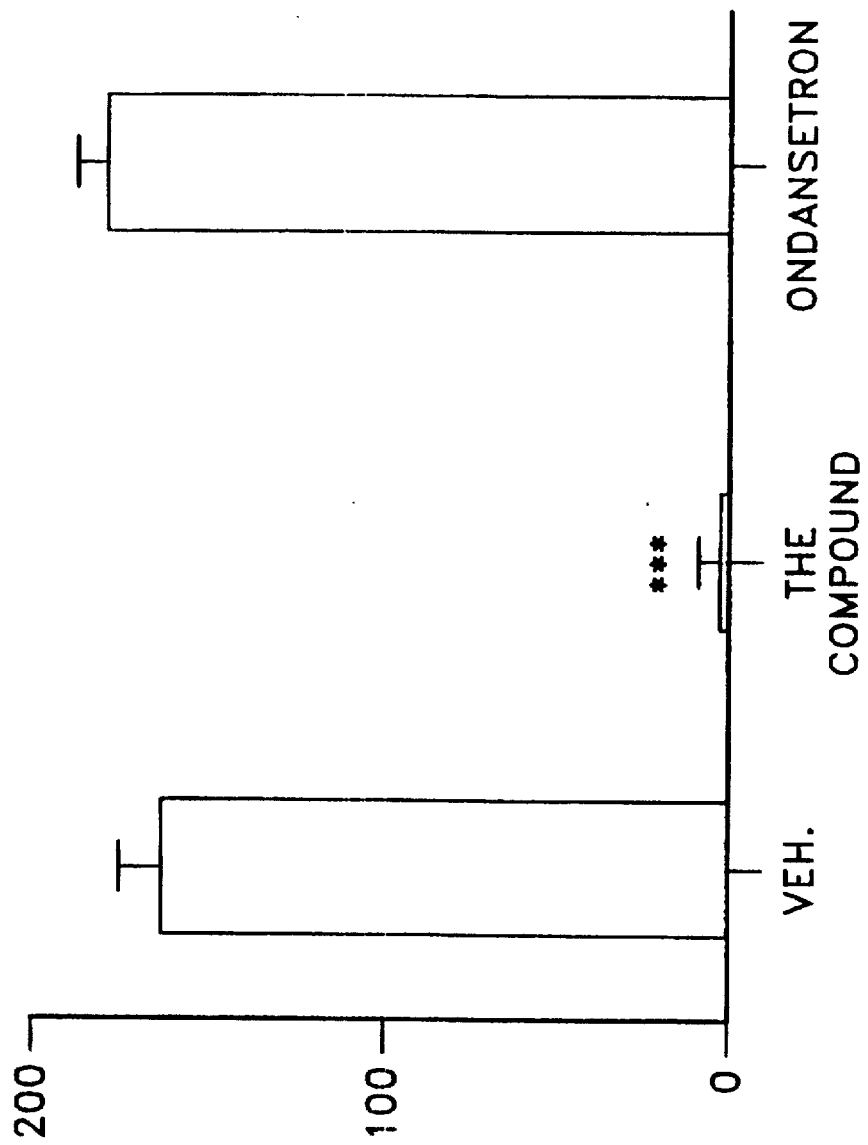
FIG. 2b is Day 1 (start of delayed emesis 3–24 hours).
Figure 2D:
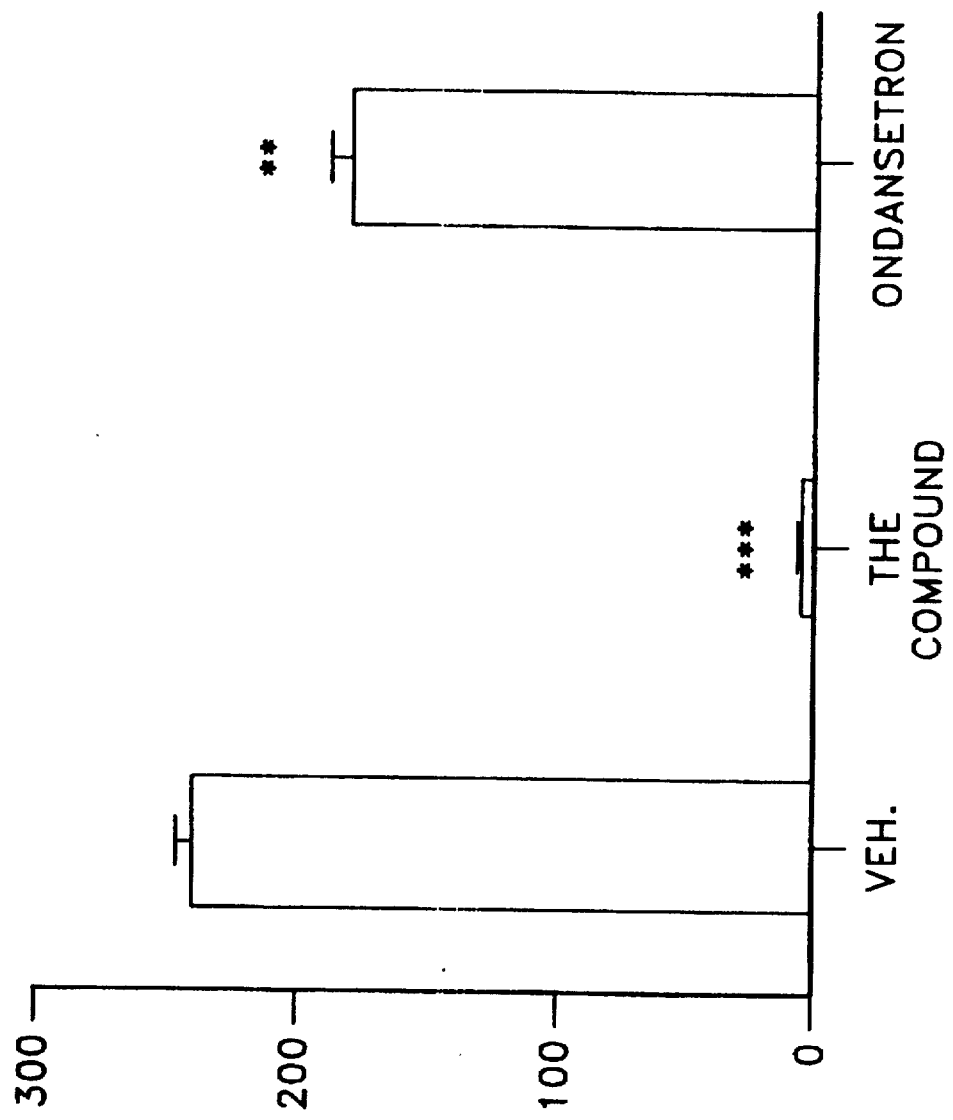
FIG. 2d is Day 3 (48–72 hours).

Cisplatin 5 mg/kg, i.p. administered as a single dose induced an acute (0–3 hours) and delayed (3–72 hours) emetic response in the ferret (FIG. 2). The Compound (10 mg/kg) or ondansetron (1 mg/kg) administered i.p. three times a day (first dose was given 1 hour before cisplatin) completely blocked the retching and vomiting during the first 3 hours of the emetic response (FIG. 2). The Compound also completely blocked the delayed emesis observed during the 3 days (FIG. 2). In contrast, the $5-HT_3$ receptor antagonist displayed much lower activity against the delayed response (FIG. 2). It failed to show any effect during the start of the delayed response and produced approximately 20% to 50% antagonism on Days 2 and 3 (FIG. 2).

These data indicate that The Compound has an improved antiemetic profile compared with ondansetron. It is able to reduce cisplatin-induced emesis in the ferret during both the acute and delayed phase.

The Compound readily penetrates into the CNS as indicated by the centrally $NK_1$ receptor mediated foot-tapping response in the gerbil and by studies determining brain concentrations in the rat.

$|Sar^9, Met(O_2)^{11}|$ substance P-Induced Hind Foot Tapping in the Gerbil

Figure 3A:
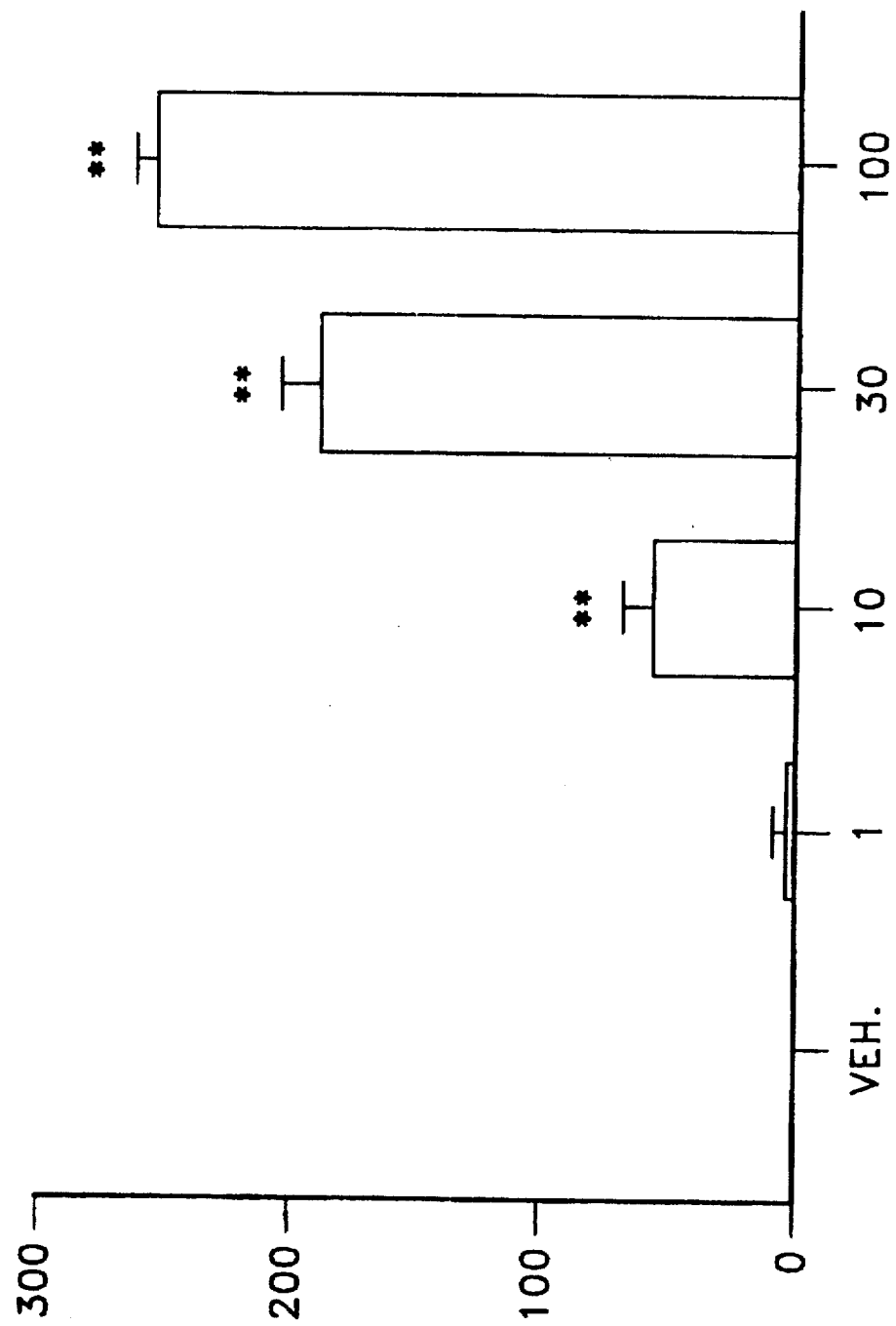
FIG. 3. Effect of The Compound on [Sar$^9$, Met(O$_2$)$^{11}$]-substance P-induced foot tapping in the gerbil. Top panel (FIG. 3a) shows dose response to [Sar$^9$, Met(O$_2$)$^{11}$] substance P following (nMol, i.c.v.) administration. The duration of foot tapping (sec) was recorded for 5 minutes immediately following recovery of the animals righting reflex. Lower panel shows the effect of The Compound on this response following s.c. administration 30 minutes before [Sar$^9$, Met(O$_2$)$^{11}$]substance P (30 nmol/animal). Results are shown as the mean (vertical bars show SEM) of 8–10 animals per group. *P<0.05, **P<0.01, Significantly different from the vehicle (Veh.) treated control group.
Figure 3B:
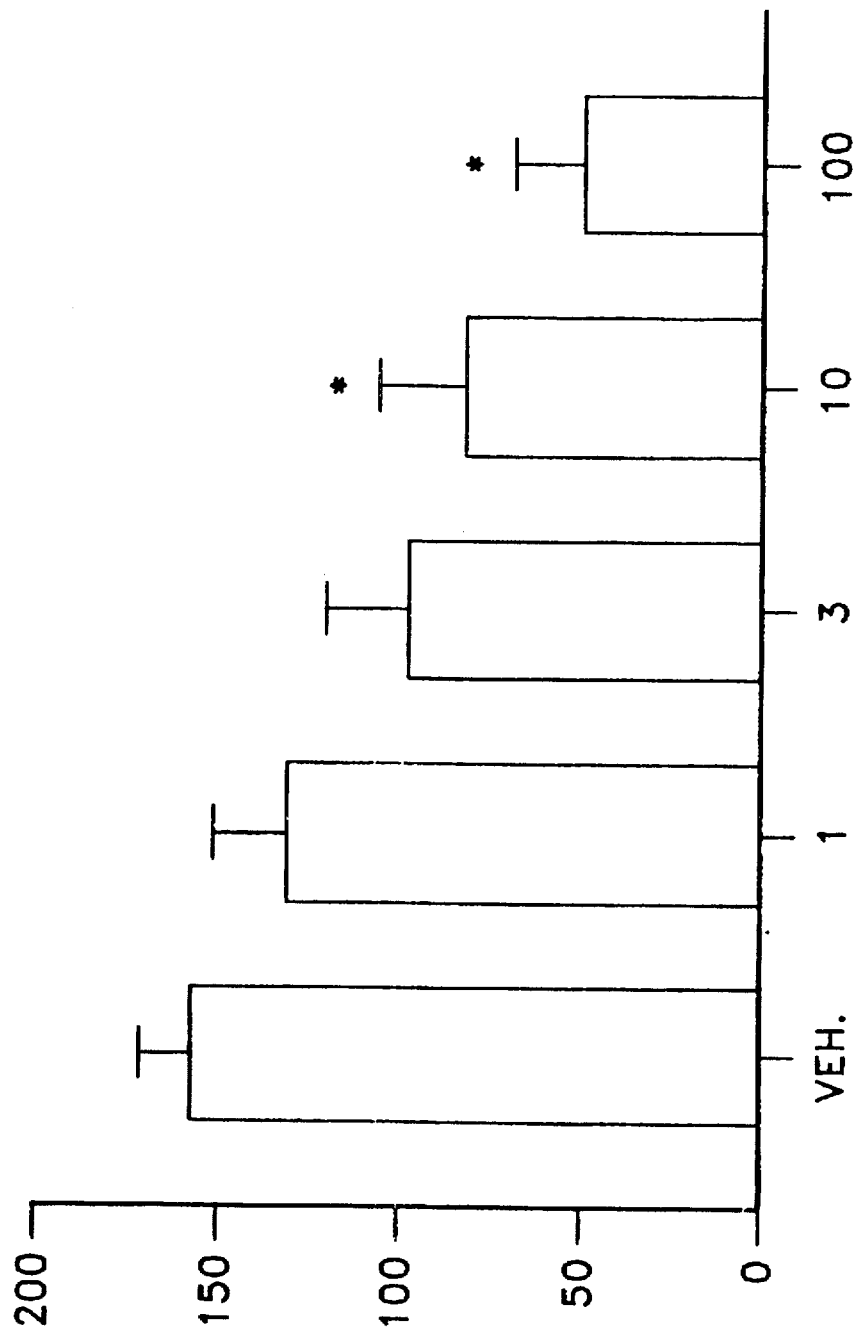

The ability of The Compound to block the centrally $NK_1$ receptor mediated foot-tapping response was examined in the gerbil to show that The Compound is able to penetrate into the brain following systemic administration. Gerbils were anaesthetized with isoflurane, and an incision was made to expose the skull. $|Sar^9, Met(O_2)^{11}|$ substance P was administered by vertical insertion of a cuffed 27-gauge needle to a depth of 4.5 mm below bregma. Animals were placed individually into observation boxes, and duration of hind foot tapping was recorded for 5 minutes immediately following recovery of the animals' righting reflex. The i.c.v. administration of the $NK_1$ receptor agonist $|Sar^9, Met(O_2)^{11}|$ substance P dose-dependently (1–100 nmol/animal) increased foot tapping, with a MED of 10 nmol (FIG. 3). The submaximal dose of 30 nmol $|Sar^9, Met(O_2)^{11}|$ substance P was chosen for antagonism studies.

Studies have shown that CP-99,994 administered systemically 30 minutes before $|Sar^9, Met(O_2)^{11}|$-substance P, can dose-dependently inhibit the foot-tapping response. It has been shown that this $NK_1$ receptor antagonist can readily penetrate into the CNS. In contrast, Dimethylamino-acetic acid 2-[2-(benzofuran-2-ylmethoxycarbonylamino)-3-(1H-indol-3-yl)-2-methyl-propionylamino]-2-phenyl-ethyl ester (Compound 2) (1–100 mg/kg) when administered s.c. failed to block this response. This is consistent with the inability of Compound 2 to block cisplatin-induced emesis in the ferret. However, Compound 2 dose-dependently antagonized the foot-tapping response following i.c.v. administration with a MED of 10 µg/animal. These data suggest that the gerbil foot-tapping response is a useful model for measuring CNS actions of $NK_1$ receptor antagonists.

The effect of The Compound on apomorphine and copper sulphate-induced emesis was studied in the ferret. The Compound was administered i.p. in PEG-200. It was found that the vehicle at the injection volume of 1 mL/kg caused an emetic response. This vehicle-induced emetic response was completely antagonized by The Compound (10 mg/kg; 1 mL/kg). Further studies showed that reducing the injection volume of PEG-200 to 0.5 mL/kg significantly decreased the vehicle emetic response. Therefore, dose-response studies with The Compound were carried out using this injection volume.

Figure 4A:
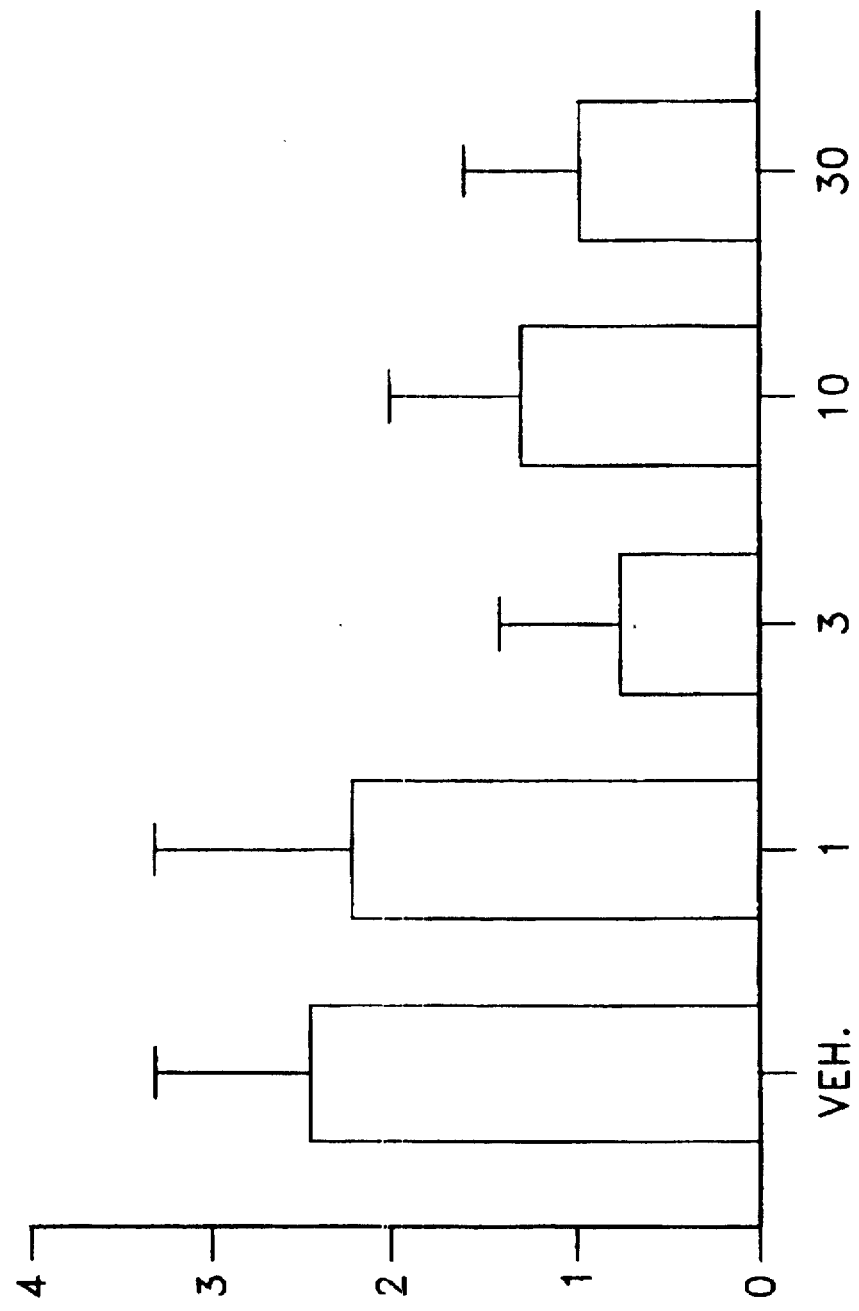
Figure 4B:
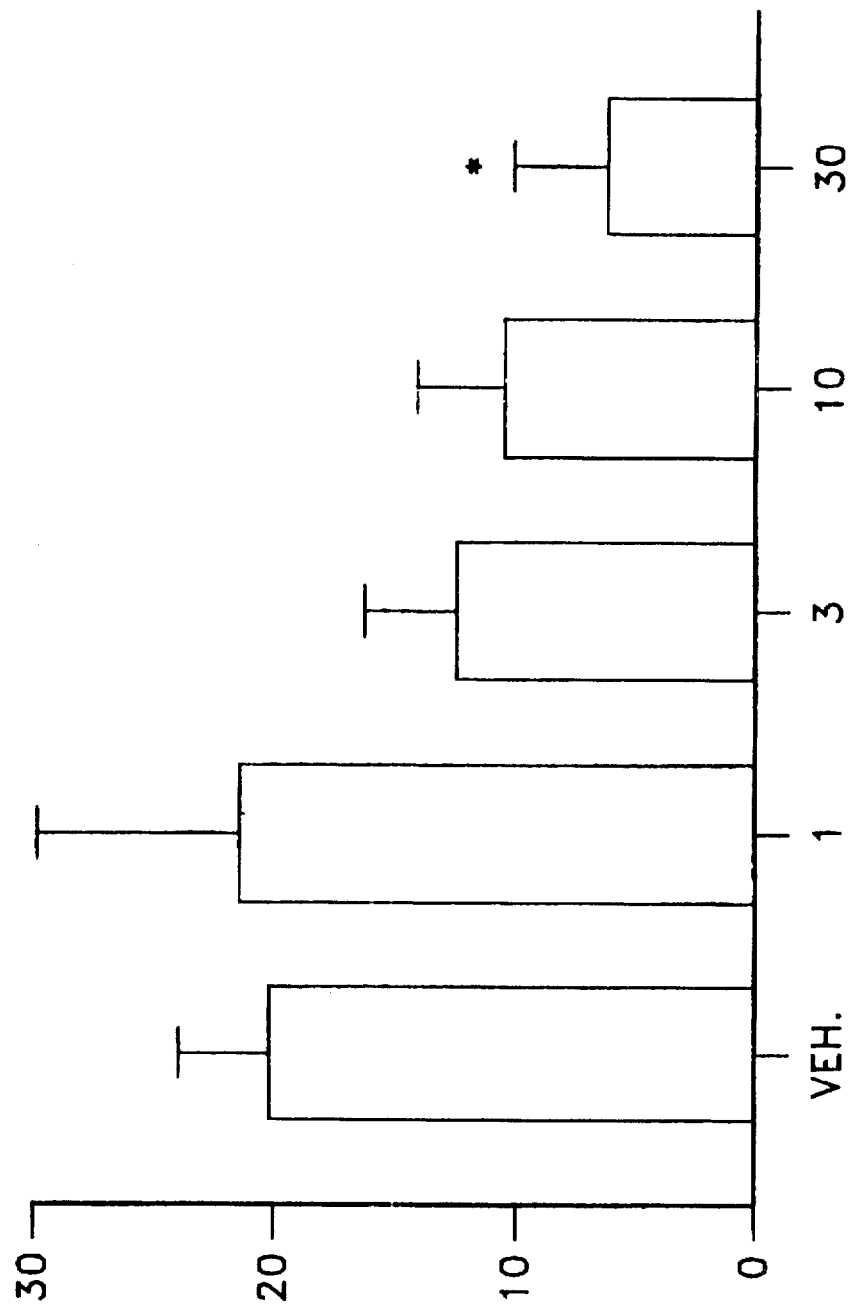
Figure 5A:
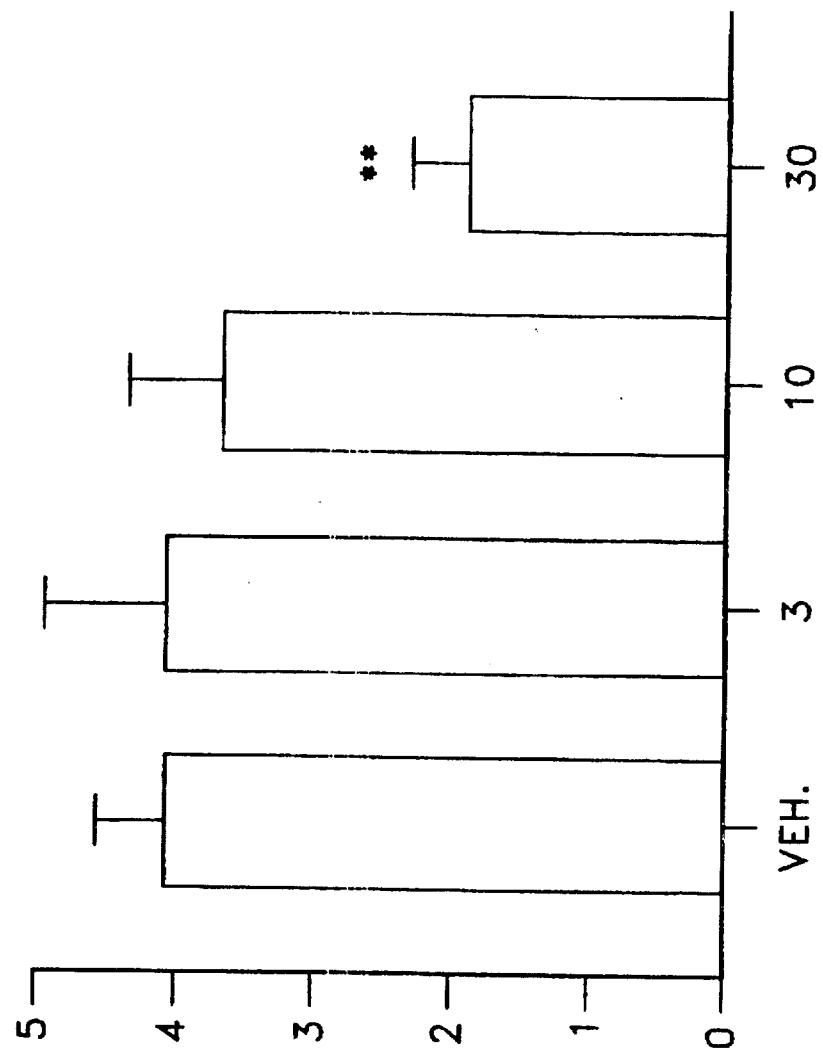
FIGS. 5a, 5b, and 5c are vomits, retches, and episodes, respectively.
Figure 5B:
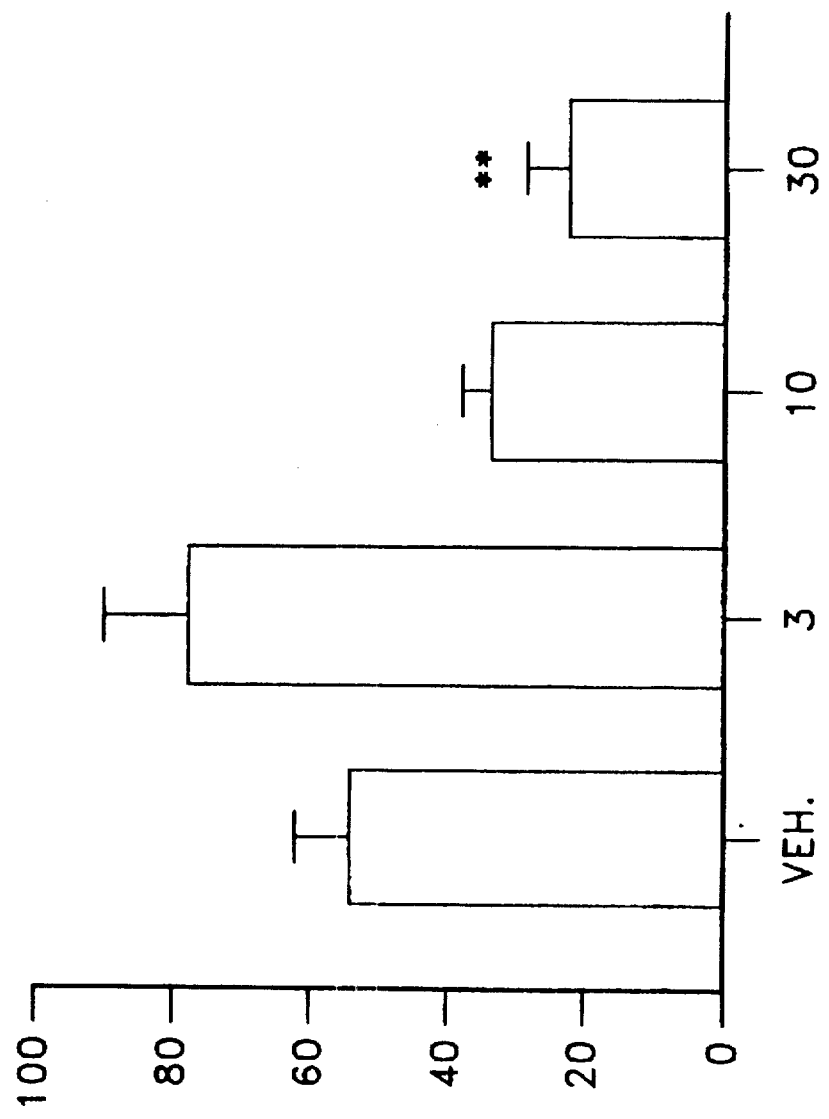
Figure 5C:
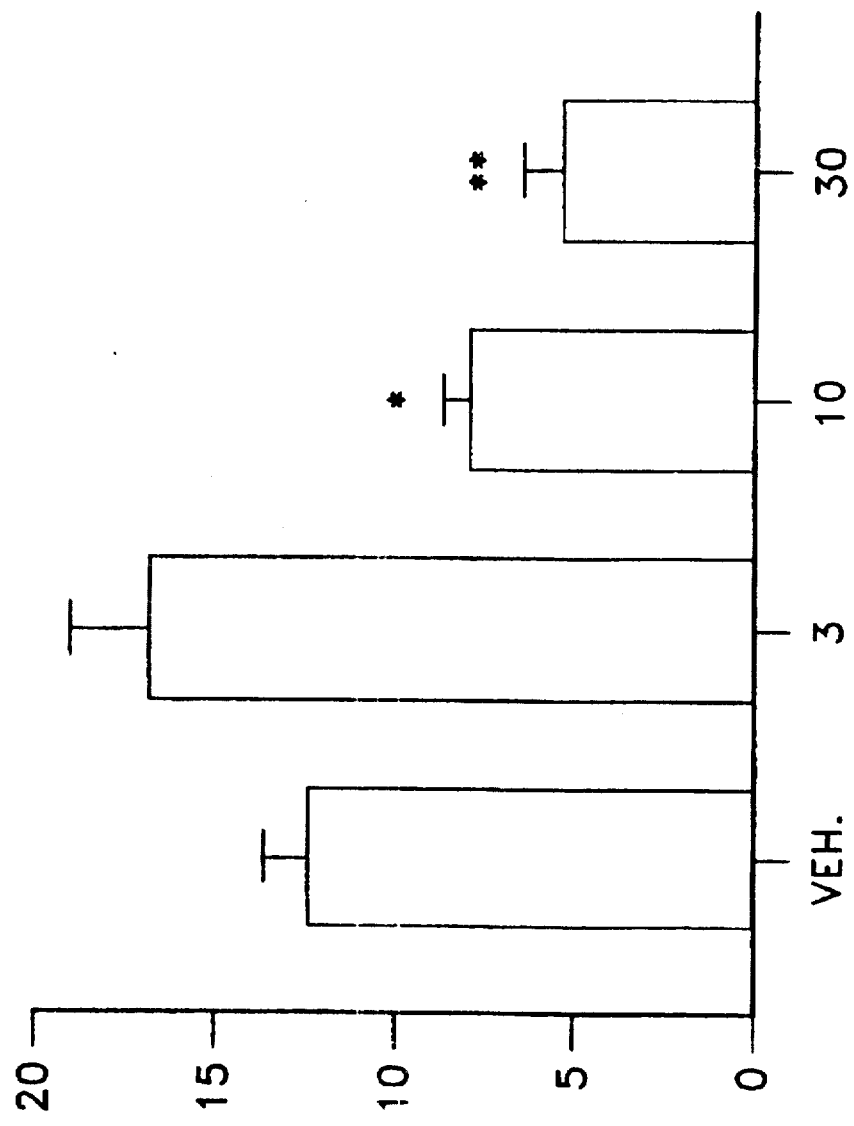

For the antagonism studies The Compound was administered 1 hour before either apomorphine (0.25 mg/kg, s.c.) or copper sulphate (12.5 mg/kg, p.o.). Animals were observed for 1 hour or 2 hours, respectively. The Compound dose-dependently (1–30 mg/kg, s.c.) reduced emesis induced by the central (apomorphine) and peripheral (copper sulphate) stimuli with a MED of 30 mg/kg (FIGS. 4 and 5).

These data show that The Compound has better antiemetic profile compared with ondansetron. It is expected to possess a broad spectrum of antiemetic activity as demonstrated by its ability to block emesis induced by both central and peripheral stimuli.

In summary, The Compound possesses antiemetic activity. IT dose-dependently (3–30 mg/kg, i.p.) blocked the frequency of vomiting and retching in ferrets induced by cisplatin (10 mg/kg, i.p.) with a minimum effective dose of 3 mg/kg. At the highest dose, it completely antagonized the emetic response.

Duration studies with The Compound (10 mg/kg, s.c. in PEG-200) in the foot-tapping model revealed that the peak antagonism of foot tapping occurs at the 0.5 hour pretreatment time. Dose-response analysis carried out at this pretreatment time showed that The Compound dose-dependently (1–100 mg/kg, s.c.) antagonized the response with a MED of 10 mg/kg (FIG. 3). This shows that The Compound is able to penetrate into the brain following systemic administration.

The Compound displayed good pharmacokinetic profile in the rat. The absolute oral bioavailability in the nanosuspension and PEG/EtOH/Water vehicles was 47% to 49%.

The oral bioavailability of The Compound was examined in the rat using PEG-400/EtOH/Water, 0.5% methyl cellulose, and nanosystem vehicle. The drug was administered either PO by gavage or IV via jugular vein. Blood samples were drawn from jugular vein cannulac into syringes containing heparin before dosing and at different times up to 24 hours postdose. Plasma was harvested by centrifugation and stored at −20° C. until analysis. Plasma samples were analyzed for The Compound using a validated liquid chromatographic method. A summary of mean (±SD) The Compound pharmacokinetic parameters following single doses of The Compound in the three vehicles is given in Table 1. The absolute oral bioavailability of The Compound from the nanosuspension formulation was 47 (±13)%, which is 10-fold greater than that resulting from a conventional suspension of The Compound in methyl cellulose and is equivalent to that from a solution of The Compound in PEG-400/EtOH/Water.

TABLE 1

Summary of Mean (±SD) The Compound Pharmacokinetic Parameters in Fasted Male Wistar Rats Following Single Doses of The Compound Administered as a Nanoparticulate Suspension(NANOSUSPENSION), a Solution of PEG-400/EtOH/Water (PEG-400) or as a Conventional Suspension in 0.5% Methyl Cellulose (MC)

| Parameter | NANOSUSPENSION | | PEG-400 | | MC |
| --- | --- | --- | --- | --- | --- |
| | IV | PO | IV | PO | PO |
| N | 4 | 4 | 4 | 4 | 4 |
| Dose (mg/kg) | 4.6 | 18.4 | 5 | 20 | 3.7 |
| Cmax (ng/mL) | — | 643(±107) | — | 774(±220) | 15.1(±5.7) |
| tmax (h) | — | 2.3(±0.4) | — | 5.0(±1.2) | 3.5(±1.9) |
| t½(h) | 4.8(±0.6) | 2.5(±0.3) | 3.5(±1.0) | 3.0(±0.4) | 2.8(±1.2) |
| AUC (ng · h/mL) | 2794(±318) | 5221(±1267) | 3556(±771) | 6956(±1450) | 107(±49) |
| Cl (mL/min/kg) | 27.8(±2.9) | — | 23.9(±4.4) | — | — |
| Vd (l/kg) | 3.7(±0.7) | — | 3.0(±1.3) | — | — |
| % F | — | 47(±13) | — | 49(±15) | 4.1(±2.1) |

Cmax = Maximum observed drug plasma concentration (ng/mL).
tmax = Time to reach Cmax (h).
t½ = Terminal elimination half-life, harmonic mean (h).
AUC = Area under the plasma concentration-time curve from zero to infinite time (ng · h/mL).
CL = Total systemic clearance (mL/min/kg).
Vd = Steady-state volume of distribution (l/kg).
% F = Absolute oral bioavailability based on ratio of dose normalized mean PO and IV AUC values.

Measurement of Brain Penetration in the Rat Using HPLC Assay

Brain penetration of The Compound was evaluated in the rat using HPLC assay. The Compound was administered either IV (4.5 mg/kg) by tail vein or PO (21.4 mg/kg) by gavage as a solution in PEG-400/Ethanol/Water. Three rats were used for each time point. Prior to blood and brain sampling, rats were anesthetized with ether. Blood samples were collected by cardiac puncture. After transcardiac perfusion with normal saline, whole brains were collected. Plasma and brain samples were analyzed using liquid chromatographic florescence detection methods. The results show that the penetration of The Compound following IV administration into the brain is fast (Table 2). For the brain, concentration of The Compound was highest (1400 ng/g) at the first sampling time of 15 minutes (Table 2) after IV injection and at 2 hours following PO administration (Table 3). Total amount in brain at these times was respectively 2.5 and 0.04 μg (Tables 2 and 13). Brain to plasma concentration ratio after IV administration was highest (1.8) at 15 minutes and then decreased to a steady value approximately 0.5 at later postdose times (Table 2).

TABLE 2

Mean (±SD) Brain and Plasma The Compound Concentrations and Ratios in Rats After IV Bolus Dose of 4.5 mg/kg in Solution of PEG-400/EtOH/Water

| Time (h) IV | Brain Conc. (BC; ng/g) | Plasma Conc. (PC; ng/mL) | BC/PC Ratio | Amount in Brain (ng) | % Dose in Brain |
|---|---|---|---|---|---|
| 0.25 | 1448 ± 456 | 819 ± 87 | 1.81 ± 0.67 | 2711 ± 668 | 0.235 ± 0.051 |
| 2 | 57 ± 4.5 | 124 ± 17 | 0.47 ± 0.11 | 114 ± 8.6 | 0.0098 ± 0.0004 |
| 4 | 20 ± 1.9 | 43 ± 5.6 | 0.47 ± 0.05 | 40 ± 3.4 | 0.0033 ± 0.0003 |
| 8 | 4.8* | 5.6 ± 3.3 | 0.52 | 9.6 | 0.0078 |
| 12 | — | 4.0 ± 1.1 | — | — | |

N = 3 rats per time point.
*N = 1.

TABLE 3

Mean (±SD) Brain and Plasma The Compound Concentrations and Ratios in Rats After PO Dose of 21.4 mg/kg in Solution of PEG-400/EtOH/Water

| Time (h) PO | Brain Conc. (BC; ng/g) | Plasma Conc. (PC; ng/mL) | BC/PC Ratio | Amount in Brain (ng) | % Dose in Brain |
|---|---|---|---|---|---|
| 0.25 | 31 ± 17 | 126 ± 92 | 0.27 ± 0.06 | 57 ± 31 | 0.00095 ± 0.00053 |
| 2 | 96 ± 79 | 301 ± 244 | 0.30 ± 0.03 | 189 ± 156 | 0.00291 ± 0.0024 |
| 4 | 212 ± 168 | 642 ± 433 | 0.29 ± 0.09 | 410 ± 333 | 0.0064 ± 0.0052 |
| 8 | 41 ± 38 | 108 ± 80 | 0.33 ± 0.11 | 81 ± 73 | 0.0013 ± 0.0012 |
| 12 | 15 ± 5 | 45 ± 20 | 0.41 ± 0.27 | 30 ± 11 | 0.00047 ± 0.00017 |

N = 3 rats per time point.

A wide range of receptor binding assays showed that The Compound possesses a high degree of selectivity for the tachykinin $NK_1$ receptor.

In side effect liability studies, The Compound up to very high doses (100 mg/kg s.c.) failed to induce sedation or ataxia in the hamster or mouse. It also failed to affect the blood pressure and heart rate of anaesthetized guinea-pigs (0.1–1.0 mg/kg, i.v.) or stimulate secretion of pancreatic amylase in the rat (0.01–10 mg/kg, i.v.).

For preparing pharmaceutical compositions from the compounds of this invention, inert, pharmaceutically acceptable carriers can be either solid or liquid. Solid form preparations include powders, tablets, dispersible granules, capsules, cachets, and suppositories.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active component is mixed with the carrier having the necessary binding properties in suitable proportions and compacted in the shape and size desired.

For preparing suppository preparations, a low-melting wax such as a mixture of fatty acid glycerides and cocoa butter is first melted and the active ingredient is dispersed therein by, for example, stirring. The molten homogeneous mixture is then poured into convenient sized molds and allowed to cool and solidify.

The powders and tablets preferably contain 5% to about 70% of the active component. Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The compounds of the invention include solvates, hydrates, pharmaceutically acceptable salts, and polymorphs (different crystalline lattice descriptors) of The Compound.

Cyclodextrin is one suitable inclusion in a pharmaceutical preparation.

The term "preparation" is intended to include the formulation of the active component with encapsulating material as a carrier providing a capsule in which the active component (with or without other carriers) is surrounded by a carrier which is thus in association with it. Similarly, cachets are included.

Tablets, powders, cachets, and capsules can be used as solid dosage forms suitable for oral administration.

Liquid form preparations suitable, for example, for intravenous administration include solutions, suspensions, and emulsions. Sterile water or water-propylene glycol solutions of the active compounds may be mentioned as an example of liquid preparations suitable for parenteral administration. Liquid preparations can also be formulated in solution in aqueous polyethylene glycol solution.

Aqueous solutions for oral administration can be prepared by dissolving the active component in suitable solvent and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

Preferably, the pharmaceutical preparation is in unit dosage form. In such form, the preparation is divided into unit doses containing appropriate quantities of the active component. The unit dosage form can be a packaged preparation, the package containing discrete quantities of the preparation, for example, packeted tablets, capsules, and powders in vials or ampoules. The unit dosage form can also be a capsule, cachet, or tablet itself, or it can be the appropriate number of any of these packaged forms.

We claim:

1. A method for the treatment of emesis in a mammal comprising administering a therapeutically effective amount of a compound named [R,S]-[2-(1H-Indol-3-yl)-1-methyl-1-(1-phenyl-ethylcarbamoyl)-ethyl]-carbamic acid benzofuran-2-ylmethyl ester to said mammal.

2. A method according to claim 1 wherein emesis is acute.

3. A method according to claim 1 wherein emesis is delayed.

4. A method according to claim 1 wherein the emesis is induced by a cancer-chemotherapeutic.

5. A method according to claim 1 wherein the emesis is induced by cisplatin during both the acute and delayed phase.

6. A method for the treatment of motion sickness in a mammal comprising administering a therapeutically effective amount of a compound named [R,S]-[2-(1H-Indol-3-yl)-1-methyl-1-(1-phenyl-ethylcarbamoyl)-ethyl]-carbamic acid benzofuran-2-ylmethyl ester.

7. A method for the treatment of post-operative nausea and vomiting in a mammal comprising administering a therapeutically effective amount of a compound named [R.S]-[2-(1H-Indol-3-yl)-1-methyl-1-(1-phenyl-ethylcarbamoyl)-ethyl]-carbamic acid benzofuran-2-ylmethyl ester to said mammal.

* * * * *